United States Patent
Alexandrov et al.

(10) Patent No.: US 8,041,090 B2
(45) Date of Patent: Oct. 18, 2011

(54) METHOD OF, AND APPARATUS AND COMPUTER SOFTWARE FOR, PERFORMING IMAGE PROCESSING

(75) Inventors: Yuriy Alexandrov, Cardiff (GB); Iain Bye, Munich (DE); Geert Kalusche, Mannedorf (CH)

(73) Assignee: GE Healthcare UK Limited, Amersham (GB)

( * ) Notice: Subject to any disclaimer, the term of this patent is extended or adjusted under 35 U.S.C. 154(b) by 824 days.

(21) Appl. No.: 12/065,744

(22) PCT Filed: Aug. 16, 2006

(86) PCT No.: PCT/GB2006/003118
§ 371 (c)(1),
(2), (4) Date: May 16, 2008

(87) PCT Pub. No.: WO2007/028944
PCT Pub. Date: Mar. 15, 2007

(65) Prior Publication Data
US 2008/0219529 A1 Sep. 11, 2008

(30) Foreign Application Priority Data

Sep. 10, 2005 (GB) .................................. 0518531.9
Mar. 16, 2006 (GB) .................................. 0605285.6

(51) Int. Cl.
*G06K 9/00* (2006.01)
*G06K 9/20* (2006.01)

(52) U.S. Cl. ............ 382/128; 382/133; 382/224; 435/4; 702/19; 702/21

(58) Field of Classification Search .......... 382/128–133, 382/203, 206, 224, 286; 435/4; 702/19–21
See application file for complete search history.

(56) References Cited

U.S. PATENT DOCUMENTS

| | | | |
|---|---|---|---|
| 6,345,115 B1 | 2/2002 | Ramm et al. | |
| 6,388,788 B1 | 5/2002 | Harris et al. | |
| 6,400,487 B1 | 6/2002 | Harris et al. | |
| 6,563,653 B2 | 5/2003 | Ramm et al. | |
| 2002/0159625 A1 | 10/2002 | Elling | |
| 2004/0076999 A1 | 4/2004 | Faeldt et al. | |
| 2004/0136581 A1 | 7/2004 | Ellis et al. | |
| 2004/0229210 A1 | 11/2004 | Sabry et al. | |
| 2005/0002552 A1* | 1/2005 | Dunn et al. | 382/133 |
| 2006/0050946 A1 | 3/2006 | Mitchison et al. | |
| 2009/0034822 A1* | 2/2009 | Coleman et al. | 382/133 |

FOREIGN PATENT DOCUMENTS

DE  36 12 884  11/1986

(Continued)

*Primary Examiner* — Melissa Koval
*Assistant Examiner* — Emily Chan (57) ABSTRACT

A computer-implemented method of performing image processing for images of biological objects includes: storing definitions of a plurality of descriptors; receiving image data relating to an image of a reference population of biological objects; receiving image data relating to an image of a target population of biological objects; processing the reference population image data to obtain a reference set of measurements, containing data for each of the descriptors; processing the target population image data to obtain a target set of measurements, containing data for each of the descriptors; and selecting a combination of the descriptors on the basis of comparing the reference set with the target set to define a preferred combination of the descriptors for use in identifying characteristics of a further population of biological objects which are similar to those of the target population.

13 Claims, 6 Drawing Sheets

FOREIGN PATENT DOCUMENTS

| | | |
|---|---|---|
| WO | WO 01/32913 | 5/2001 |
| WO | WO 02/097714 | 12/2002 |
| WO | WO 2004/088574 | 10/2004 |
| WO | WO 2005/010677 | 2/2005 |
| WO | WO 2006/001843 | 1/2006 |
| WO | WO 2006/008542 | 1/2006 |

* cited by examiner

METHOD OF, AND APPARATUS AND COMPUTER SOFTWARE FOR, PERFORMING IMAGE PROCESSING

CROSS-REFERENCE TO RELATED APPLICATIONS

This application is a filing under 35 U.S.C. §371 and claims priority to international patent application number PCT/GB2006/003118 filed Aug. 19, 2006, published on Mar. 15, 2007, as WO 2007/028944, which claims priority to British patent application numbers 0518531.9 filed Sep. 10, 2005 and 0605285.6 filed Mar. 16, 2006.

FIELD OF THE INVENTION

The present invention relates to a computer-implemented method of performing image processing and population analysis, in particular to performing processing for an image of biological objects. The present invention further relates to apparatus and computer software arranged to perform the image processing.

BACKGROUND OF THE INVENTION

There is currently a need in drug discovery and in general biological research for methods and apparatus for accurately performing cell-based assays. Cell-based assays are advantageously employed for assessing the biological activity of chemical compounds.

In addition, there is a need to quickly and inexpensively screen large numbers of chemical compounds. This need has arisen in the pharmaceutical industry where it is common to test chemical compounds for activity against a variety of biochemical objects, for example, receptors, enzymes and nucleic acids. These chemical compounds are collected in large libraries, sometimes exceeding one million distinct compounds.

Performing cell-based assays typically involves recording cellular images and quantifying these images using algorithms of image analysis software. Instruments are known for imaging fluorescently labelled cells and software of these instruments have a number of analysis modules which quantify, for example, biological protein translocations and reactions to stimuli of cellular pathways within the fluorescently labelled cells.

Such instruments typically require a user to initially set up image processing software parameters to recognise cells having particular characteristics. In order for a user to correctly train the software, the user needs to be trained to a required standard, which is often a time consuming, complex and expensive procedure. A lack of user training can result in poor output data leading to an inefficient use of the technology for biocellular analysis.

The article with reference: 'Location Proteomics; Providing Critical Information for Systems Biology', G.I.T. Imaging and Microscopy 2/2005, describes use of subcellular location features to cluster images into sets. Images with similar patterns of protein locations may be grouped together automatically without human assistance.

International patent application WO 2002097714 describes an expert system and software method for image recognition optimised for the repeating patterns characteristic of organic material. The method is performed by computing parameters across a two dimensional grid of pixels. The parameters are fed to multiple neural networks, one for each parameter, which have been trained with images. Each neural network then outputs a measure of similarity of the unknown material to the known material on which the network has been trained. However, using a neural network makes it difficult for a user to adjust the system and influence the outcomes of the analyses.

International patent application WO 2004088574 and scientific poster entitled 'Learning Algorithms Applied to Cell Subpopulation Analysis in High Content Screening', by Bohdan Soltys, Yuriy Alexandrov, Denis Remezov, Marcin Swiatek, Louis Dagenais, Samantha Murphy and Ahmad Yekta describe a method of classifying biological cells into cellular subpopulations. A user supervises creation of a 'training data set' by selecting individual cells from an image and classifying the selected cells into a particular subpopulation. Thus, the user determines which, and how many, cellular descriptors are best for classifying the cells. The training data set includes classification data which identifies characteristics of cells of a certain subpopulation. The training data set is subsequently applied to a cellular image to identify and classify further cells without user supervision. When a large set of descriptors is used, the classification process becomes a time consuming and complicated task. In order to provide successful training, the size of the training data set should grow exponentially with the number of used descriptors. This is known as the "curse of dimensionality", as described by Trevor Hastie, Robert Tibshirani and Jerome Friedman in the publication "The Elements of Statistical Learning" at page 25. The use of supervised classification methods for cellular assays is therefore relatively limited.

International patent application WO 2006001843 describes a system for characterising a multidimensional distribution of responses from the objects in a population subject to a perturbation. The methods enable the creation of a "degree of response" scale interpolated from non-perturbed and perturbed reference populations. A "fingerprint" of an object, such as a cell, is measured in terms of a feature vector, namely a vector of descriptor values that characterise the object. However, the manner of selection of features that constitute a fingerprint in any particular application is not disclosed.

It is an object of the present invention to provide a more automated and efficient method of setting up a system for performing image and data analysis, in particular for systems that typically contain several populations of biological objects.

SUMMARY OF THE INVENTION

In accordance with the present invention, there is provided a computer-implemented method of performing image processing for images of biological objects, said method including:

a) storing definitions of each of a plurality of descriptors for which measurements can be taken in relation to said biological objects; said plurality of descriptors is synonymous to "feature space", the term used in pattern recognition literature b) receiving image data relating to an image of a reference population of biological objects exposed to a given biological environment;

c) receiving image data relating to an image of a target population of biological objects exposed to a different given biological environment;

d) processing said reference population image data to obtain set of measurements for each of said plurality of descriptors (reference measurements data);

e) processing said target population image data to obtain set of measurements for each of said plurality of descriptors (target measurements data); and f) selecting a combination of one or more of said plurality of descriptors on the basis of comparing said reference measurements data with said target measurements data to define a preferred combination of said descriptors for use in identifying characteristics of a further population of biological objects which are similar to those of the target population.

The preferred combination includes a preferred selection of the descriptors for use in processing images of further populations of biological objects, such as biological cells, having similar characteristics to the objects of the target population. Characteristics of objects of the further population may therefore be identified. Each of the measurements of the reference and target sets are taken for at least one of the plurality of descriptors.

Defining the preferred combination in accordance with the present invention may be a fully automated procedure, without needing a user to initially train an image processing system by identifying particular cells and/or cellular characteristics of a population of cells. This significantly reduces the time taken to set up image processing apparatus for performing cellular assays, particularly when the preferred selection includes a large number of descriptors. Thus, the efficiency of processing cellular images is improved. Moreover, with the eliminated, or at least reduced, need for training of the user, costs of assaying cell samples may be reduced.

Preferably the method of the present invention provides a method which includes:

g) modifying said sets of measurements, by changing the selected combination of descriptors, h) comparing the data from reference and target populations using the measures of difference between said reference population and said target population; and i) comparing said measures of difference determined in step h) to select said preferred combination of said descriptors.

In step g), modification can be performed based on the knowledge of the response from previous data, or basing on data from modelling.

The preferred combination of descriptors may be defined using a combinatorial search, as described in the "Detailed Description of the Invention" section, below. Identifying the combination of descriptors which gives a preferred measure of difference, for example a maximum inter-cluster separation, allows the preferred combination to be defined effectively.

Further, in accordance with the present invention, selecting the combination in step f) preferably includes excluding at least one of said plurality of descriptors from said combination selected in step f), using said measurement data from reference population and said measurement data from target population, so that said preferred combination excludes at least one descriptor.

Excluding at least one of the descriptors from the preferred combination reduces a number of measurements in each set of measurements in order to, for example, improve an efficiency of performing calculations during comparison of the sets of measurements. The efficiency of defining the preferred combination may therefore be improved.

In a preferred embodiment of the present invention, said target population has been treated with a treatment agent and said reference population has not been treated with said treatment agent. The treatment agent may be a chemical entity or a physical stimulus. Examples of a suitable physical stimulus include electromagnetic radiation, such as UV or IR radiation. Examples of a chemical entity include organic and inorganic compounds. Preferably, the chemical entity is a drug candidate.

By comparing a treated population of objects with an untreated population of objects, the method of the present invention provides efficient identification of differences between characteristics of treated objects and characteristics of untreated objects. Using these differences, populations of the objects may be effectively identified.

Preferably, the method of the present invention further includes:

j) receiving further image data relating to an image of a further population of biological objects exposed to a given environment;

k) processing said further population image data to derive a set of measurements of said further population with said preferred combination of said descriptors; and l) processing said set of measurements for said further population to identify characteristics which are similar to those of said target population.

Once the preferred combination has been defined, it may be used to process images of a further population of objects. By using the preferred combination, objects having similar characteristics to the objects of the target population can be identified. Use of the preferred combination of descriptors for image processing of further populations of objects increases an efficiency of identifying objects belonging to the particular populations when performing biological assays.

Preferably, in accordance with the present invention, said processing in step l) includes classifying said objects of said further population.

Objects of further populations which are identified using the preferred combination may subsequently be classified. The improved efficiency of identifying objects of a particular population provides a more efficient classification of objects, using image data, during cellular assaying.

In accordance with a preferred embodiment of the present invention, the system does not require a user to provide input which is used to define said preferred combination of said descriptors.

Alternatively, a user may need to provide input to aid definition of the preferred combination. However, by comparison of the sets of measurements to define the preferred combination, the system of the present invention reduces any such required user input.

Further features and advantages of the invention will become apparent from the following description of preferred embodiments of the invention, given by way of example only, which is made with reference to the accompanying drawings.

DEFINITIONS

The following definitions will be adhered to in this document:

Parameter is a user-defined value used for setting up the procedure for identifying objects of interest, such as biological cells, in an image. The parameters help to perform the segmentation task, as described later. These values are typically kernel sizes, sensitivity levels, or threshold levels.

Pattern is the element, such as a biological object, which is the unit of recognition in a problem to be solved, for example a process of classifying a population of cells. A pattern is typically represented by at least one biological object, for example a cell, under investigation.

Descriptor is a measurable characteristic of a biological object or a region of interest in an image. A descriptor is the number which describes, for example, an intensity, shape, texture, spatial correlation or any other physical signature of the object of interest, which is relevant in the context of the given problem.

Feature vector includes one or more descriptors which define a feature of a population of biological objects, for example its state in the cell cycle. This ensemble of descriptors is called the feature vector. The number of descriptors that build a feature vector is called its dimension. Therefore, by way of example, a feature vector formed of three descriptors has three dimensions. In analysis of a population of biological objects, a similarity between objects is measured by using a metric of these feature vectors.

Feature space is the one-dimensional or multi-dimensional space with coordinates represented by the one or more descriptors (components) of the feature vector used in the classification problem.

Class is a semantic label assigned to at least one pattern. In cell assay applications, classes usually denote different physiological states and/or fluorescent cell phenotypes, for example the S, G1, G2 cell cycle phases.

Cluster is a set of patterns of the same class. In the present invention, clusters represent sub-populations of biological objects, for example cells residing in the G1 or S phase of the cell cycle. In the feature space, each pattern is represented by a point defined by its feature vector; therefore the set of patterns is represented by the set (cluster) of points.

Image stack is a collection of multiple images

DETAILED DESCRIPTION OF THE INVENTION

The present invention provides a computer-implemented method of performing image processing for images of biological objects, using imaging apparatus. The imaging apparatus comprises an imaging system having image processing computer software which includes functionality for performing the method of the present invention. The computer software may be provided on a data carrier such as a compact disc (CD). Embodiments of the present invention will be described below in which biological objects are biological cells.

Imaging System

Figure 1:
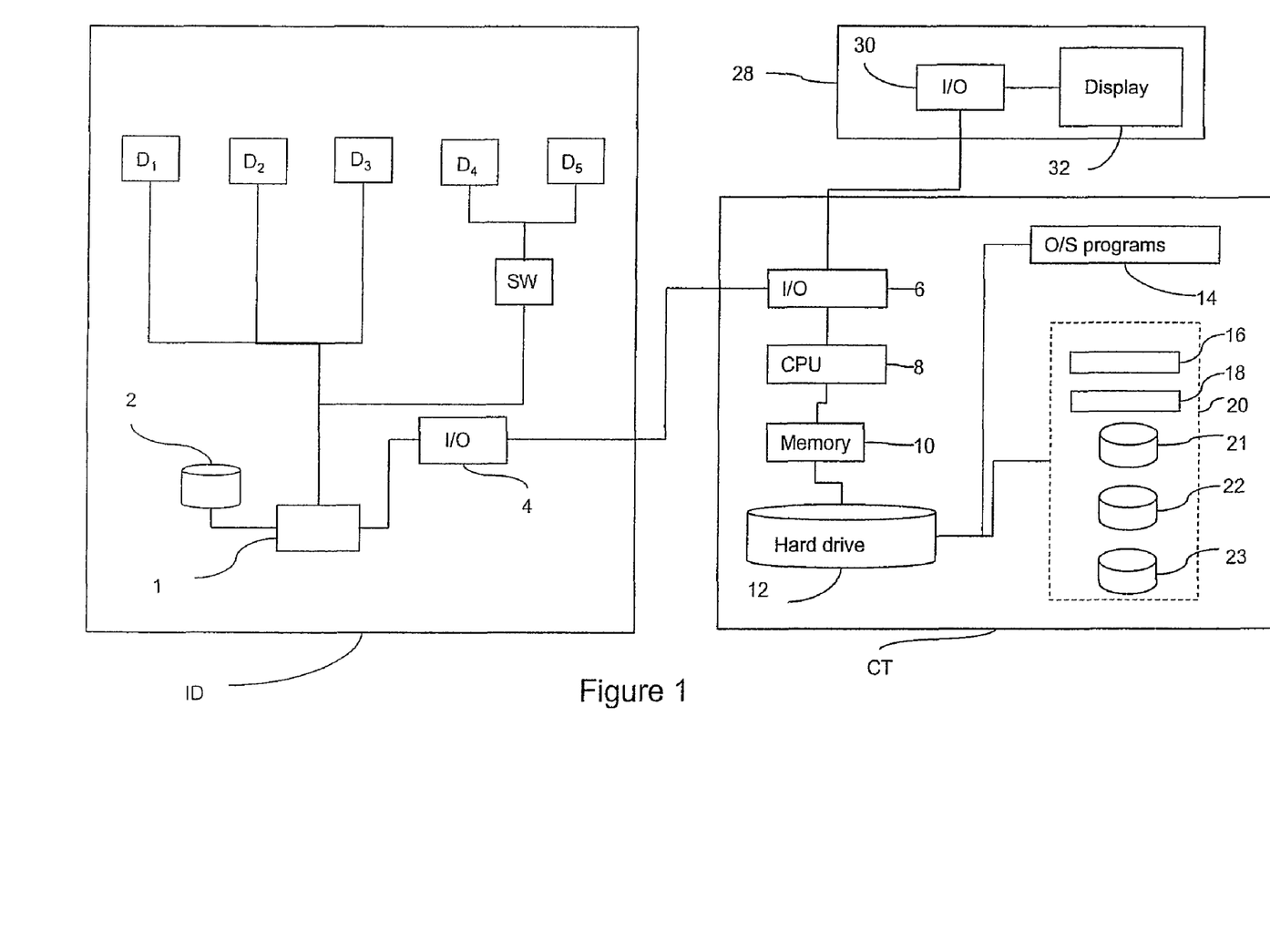
FIG. 1 is a schematic illustration showing data processing components in an imaging system arranged in accordance with an embodiment of the invention.

The imaging system will be described with reference to FIG. 1 which shows a schematic illustration of data processing components of an imaging system arranged in accordance with the invention. The system includes an imaging device ID, such as a confocal microscope, as described in further detail below, which includes detectors $D_1$, $D_2$, $D_3$, $D_4$, $D_5$, a switch SW, a control unit 1, an image data store 2 and an Input/Output (I/O) device 4. An associated computer terminal CT includes a central processing unit (CPU) 8, memory 10, a data storage device such as a hard disc drive 12 and I/O devices 6 which facilitate interconnection of the computer CT with both the imaging device ID via the I/O device 4, and a display element 32 of a screen 28 via a screen I/O device 30. Operating system programs 14 are stored on the hard disc drive 12 and control, in a known manner, low level operation of the computer terminal CT. Program files and data 20 are also stored on the hard disc drive 12, and control, in a known manner, outputs to an operator via associated devices and output data stored on the hard disc drive 12. The associated devices include the display 32 as an element of the screen 28, a pointing device (not shown) and keyboard (not shown), which receive input from, and output information to, the operator via further I/O devices (not shown). Included in the program files 20 stored on the hard drive 12 are an assay control application 16, an image processing and analysis software system 18, and a database 22 for storing image data received from the imaging device ID and output files produced during data processing. The image analysis software system 18 may be a customized version of known image processing and analysis software packages.

The performance of an assay using the imaging device ID is controlled using control application 16, and the image data are acquired. After the end of acquisition of image data for at least one well in a multi-well plate by at least one detector $D_1$, $D_2$, $D_3$, the image data are transmitted to the computer terminal CT and stored in the database 22 on the computer terminal hard drive 12, at which point the image data can be processed using the image processing and analysis software system 18, as will be described in greater detail below.

The program files and data 20 further include definitions of a plurality of descriptors, stored as hardcoded routines 21, in accordance with the method of the present invention. Further information of these descriptors is given below.

The program files and data 20 further include a descriptor data store 23 which stores historical data of relevant descriptors used for cellular image analyses. A definition of at least one preferred combination of the descriptors may also be stored.

Figure 2:
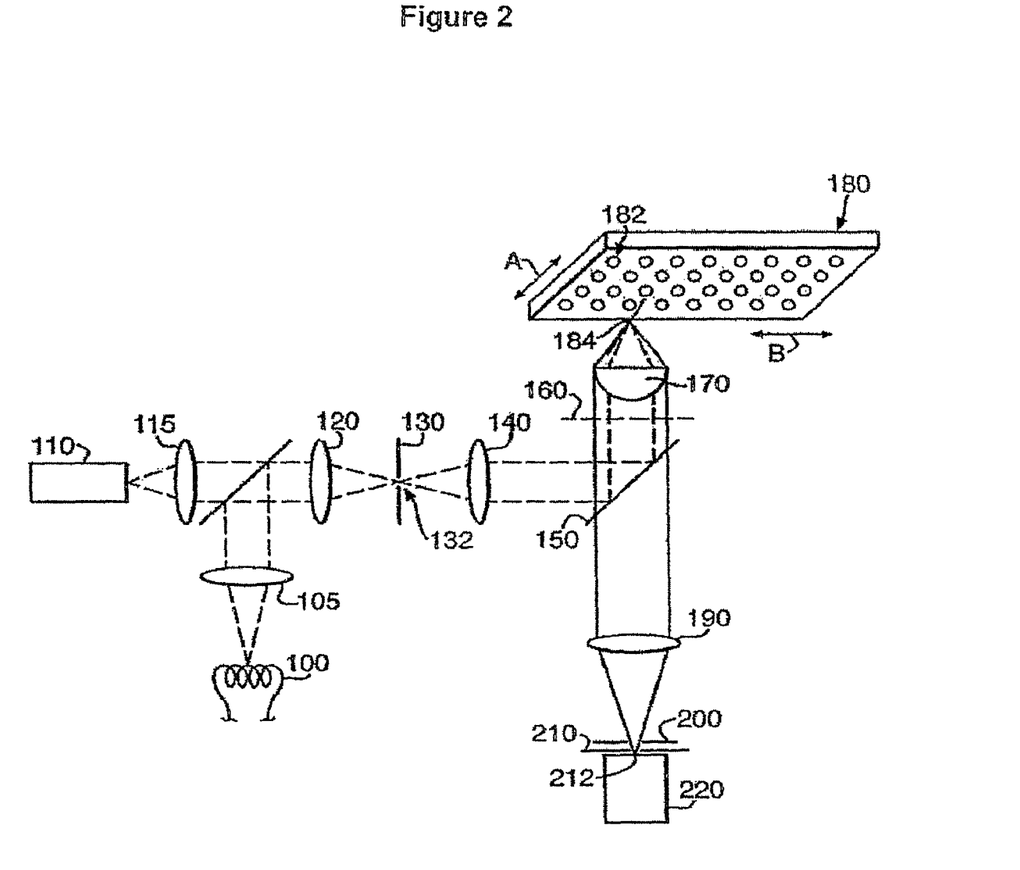
FIG. 2 is a schematic view of a line-scan confocal microscope used to image samples according to an embodiment of the present invention.

FIG. 2 shows an embodiment of the present invention, where the imaging device ID used is a confocal microscope based on the GE Healthcare Bio-Sciences IN Cell Analyzer 3000 system. The microscope comprises a source 100 or 110 of electromagnetic radiation for example, in the optical range, 350-750 nm, a cylindrical lens 120, a first slit mask 130, a first relay lens 140, a dichroic mirror 150, an objective lens 170, a multi-well plate 180 containing a two-dimensional array of sample wells 182, a tube lens 190, a filter 200, a second slit mask 210 and a detector 220. These elements are arranged along optical axis OA with slit apertures 132, 212 in masks 130, 210 extending perpendicular to the plane of FIG. 2. The focal lengths of lenses 140, 170 and 190 and the spacings between these lenses as well as the spacings between mask 130 and lens 140, between objective lens 170 and multi-well plate 180 and between lens 190 and mask 210 are such as to provide a confocal microscope. In this embodiment, electromagnetic radiation from a lamp 100 or a laser 110 is focused to a line using a cylindrical lens 120. The shape of the line is optimized by a first slit mask 130. The slit mask 130 is depicted in an image plane of the optical system that is in a plane conjugate to the object plane. The illumination stripe formed by the aperture 132 in the slit mask 130 is relayed by lens 140, dichroic mirror 150 and objective lens 170 onto a multi-well plate 180 which contains a two-dimensional array of sample wells 182. For convenience of illustration, the optical elements of FIG. 2 are depicted in cross-section and the multi-well plate in perspective. The projection of the line of illumination onto multi-well plate 180 is depicted by line 184 and is also understood to be perpendicular to the plane of FIG. 2. As indicated by arrows A and B, multi-well plate 180 may be moved in two dimensions (X,Y) parallel to the dimensions of the array by means not shown.

An image of the sample area, for example a sample in a sample well 182, is obtained by projecting the line of illumination onto a plane within the sample, imaging the fluorescence emission therefrom onto a detector 220 and moving the plate 180 in a direction perpendicular to the line of illumination, synchronously with the reading of the detector 220. In the embodiment depicted in FIG. 2, the fluorescence emission is collected by the objective lens 170, projected through the dichroic beamsplitter 150, and imaged by lens 190 through filters 200 and a second slit mask 210 onto a detector 220, such as is appropriate to a confocal imaging system having an infinity-corrected objective lens 170. The dichroic beamsplitter 150 and filter 200 preferentially block light at the illumination wavelength. The detector 220 illustratively is a camera and may be either one dimensional or two dimensional. If a one dimensional detector is used, slit mask 210 is not needed. The illumination, detection and translation procedures are continued until the prescribed area has been imaged.

An embodiment enabling multi-wavelength fluorescence imaging is preferred for certain types of assays. In this way, image data can be generated for the same area being imaged in each of a plurality of different color channels simultaneously.

Figure 3A:
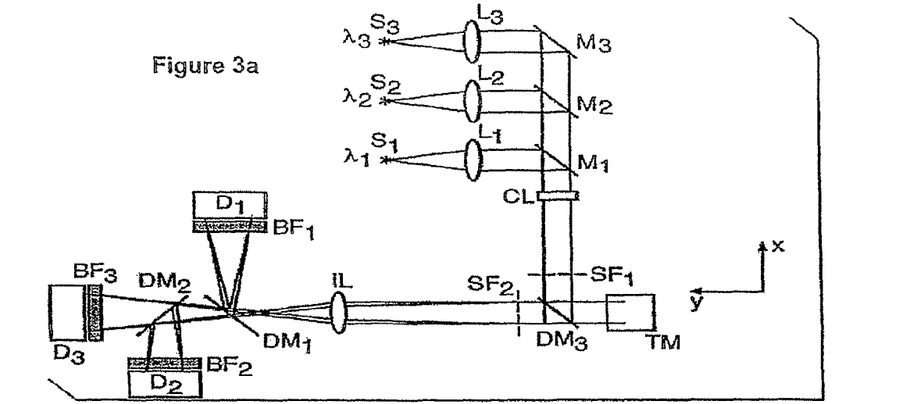
FIGS. 3A and 3B are, respectively, a top view and a side view of the ray path of a multicolor embodiment of the present invention, without a scanning mirror.
Figure 3B:
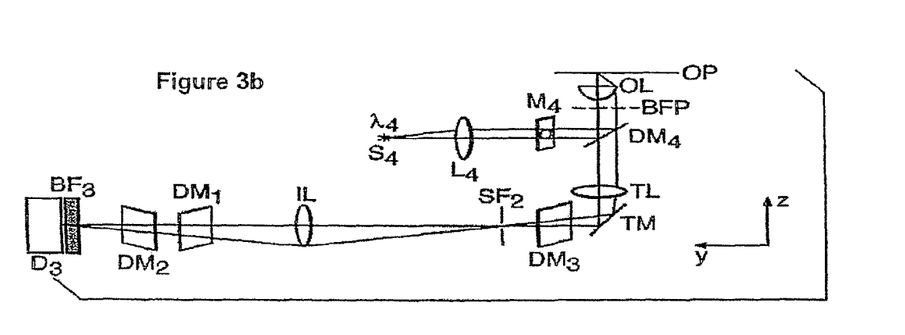
Figure 3C:
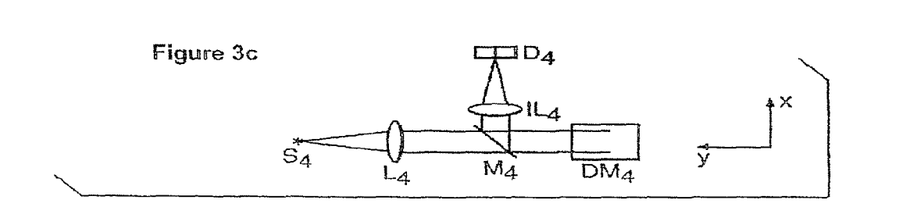
FIG. 3C is a top view of the ray path of a single beam autofocus.

The number of independent wavelengths or colors will depend on the specific assay being performed. In one embodiment three illumination wavelengths are used. FIGS. 3A and 3B depict the ray paths in a three-color line-scan confocal imaging system, from a top view and a side view respectively. In general, the system comprises several sources $S_n$ of electromagnetic radiation, collimating lenses $L_n$ and mirrors $M_n$ for producing a collimated beam that is focused by cylindrical lens CL into an elongated beam at first spatial filter $SF_1$, a confocal microscope between first spatial filter $SF_1$, and second spatial filter $SF_2$ and an imaging lens IL, beamsplitters $DM_1$ and $DM_2$ and detectors $D_n$ for separating and detecting the different wavelength components of fluorescent radiation from the sample. Spatial filters SF, and SF and $SF_2$ preferably are slit masks.

In particular, FIG. 3A depicts sources, $S_1$, $S_2$ and $S_3$, for colours $\lambda_1$, $\lambda_2$ and $\lambda_3$, and lenses $L_1$, $L_2$ and $L_3$ that collimate the light from the respective sources. Lenses $L_1$, $L_2$ and $L_3$, preferably are adjusted to compensate for any chromaticity of the other lenses in the system. Mirrors $M_1$, $M_2$ and $M_3$ are used to combine the illumination colors from sources $S_n$. The mirrors $M_2$ and $M_1$ are partially transmitting, partially reflecting and preferentially dichroic. $M_2$, for example, should preferentially transmit $\lambda_3$, and preferentially reflect $\lambda_2$. It is thus preferential that $\lambda_3$ be greater than $\lambda_2$.

Operation of the microscope in a confocal mode requires that the combined excitation beams from sources $S_n$ be focused to a "line", or a highly eccentric ellipse, in the object plane OP. As discussed in connection to FIG. 2 above, a variety of configurations may be used to accomplish this. In the embodiment depicted in FIG. 3A, the combined illumination beams are focused by cylindrical lens CL into an elongated ellipse that is coincident with the slit in the spatial filter $SF_1$. As drawn in FIGS. 3A and 3B, the slit mask $SF_1$ resides in an image plane of the system, aligned perpendicular to the propagation of the illumination light and with its long axis in the plane of the page of FIG. 3A. The lenses TL and OL relay the illumination line from the plane containing $SF_1$ to the object plane OP. A turning mirror, TM, is for convenience. In another embodiment, $DM_3$ is between TL and OL and CL focuses the illumination light directly into the BFP. Other embodiments will be evident to one skilled in the art.

Referring to FIG. 3B, the light emitted by the sample and collected by the objective lens, OL, is imaged by the tube lens, TL, onto the spatial filter, $SF_2$. $SF_2$ is preferentially a slit aligned so as to extend perpendicular to the plane of the page. Thus, the light passed by filter $SF_2$ is substantially a line of illumination. $SF_2$ may be placed in the primary image plane or any plane conjugate thereto. $DM_3$ is partially reflecting, partially transmitting and preferably "multichroic". Multi-wavelength "dichroic" mirrors or "multichroic" mirrors can be provided that preferentially reflect certain wavelength bands and preferentially transmit others.

Here, $\delta\lambda_1$ will be defined to be the fluorescence emission excited by $\lambda_1$. This will, in general, be a distribution of wavelengths somewhat longer than $\lambda_1$. $\delta\lambda_2$ and $\delta\lambda_3$ are defined analogously. $DM_3$ preferentially reflects $\lambda_n$, and preferentially transmits $\delta\lambda_n$, n=1, 2, 3. The light transmitted by $SF_2$ is imaged onto the detection devices, which reside in planes conjugate to the primary image plane. In FIG. 3A, an image of the spatial filter $SF_2$ is created by lens IL on all three detectors, $D_n$. This embodiment is preferred in applications requiring near-perfect registry between the images generated by the respective detectors. In another embodiment, individual lenses $IL_n$ are associated with the detection devices, the lens pairs IL and $IL_n$ serving to relay the image of the spatial filter $SF_2$ onto the respective detectors $D_n$. The light is split among the detectors by mirrors $DM_1$ and $DM_2$. The mirrors are partially transmitting, partially reflecting, and preferentially dichroic. $DM_1$ preferentially reflects $\delta\lambda_1$ and preferentially transmits $\delta\lambda_2$ and $\delta\lambda_3$. The blocking filter, $BF_1$, preferentially transmits $\delta\lambda_1$ effectively blocking all other wavelengths present. $DM_2$ preferentially reflects $\delta\lambda_2$ and preferentially transmits $\delta\lambda_3$. The blocking filters, $BF_2$ and $BF_3$, preferentially transmit $\delta\lambda_2$ and $\delta\lambda_3$ respectively, effectively blocking all other wavelengths present.

The imaging system may be the 'IN Cell Analyzer 1000' type of imaging system, manufactured by GE Healthcare Bio-Sciences, which is described in further detail in U.S. Pat. No. 6,563,653 and U.S. Pat. No. 6,345,115, the contents of each of which are incorporated herein by reference.

The imaging system may alternatively be the 'IN Cell Analyzer 3000' type of imaging system, manufactured by GE Healthcare Bio-Sciences which is described in further detail in U.S. Pat. No. 6,400,487 and U.S. Pat. No. 6,388,788, the contents of each of which are incorporated herein by reference.

Image Acquisition

Images can be recorded of a cellular sample using the imaging system. A sample cell culture may be placed in a plurality of receptacles, in this example sample wells of a multi-well microtitre plate, different chemical compounds placed in each well, and, at a desired time following the addition of the chemical compounds, image acquisition can be performed of the samples.

For embodiments of the present invention described below, the imaging system records an image of a cell culture which is a reference population of cells exposed to a given biological environment, an image of a cell culture which is a target population of cells exposed to a different given biological environment, and an image of a cell culture which is a further population of cells exposed to a given biological environment. The further population of cells has similar cellular characteristics to the target population of cells.

The given biological environments provide specific surrounding conditions to the cells, for example a specific temperature or a specific treatment agent. For embodiments of the present invention described below, the cells of the target population have been treated with a treatment agent, such as a drug, and the cells of the reference population have not been treated with the treatment agent. The cells of the reference population are of a natural, unperturbed, unchanged, unmodified state close to the physiological homeostasis. In embodiments described below, the reference population is a control population of cells which allows, by comparison of cells of the reference population with cells of the target population, any effects upon the target population cells caused by the treatment agent, to be identified.

Available Descriptors

Measurements in relation to the cells of the reference population and in relation to the cells of the target population can be taken for the plurality of descriptors. In this embodiment, such measurements are taken using the identified cellular areas of the images. Examples of definitions of the descriptors will now be given below, in relation to biological objects. Some of the descriptors below are defined in relation to pixels of the images.

I. Intensity Descriptors i) Mean Intensity. Mean intensity value of the pixels contained within the object outline.

ii) Median Intensity. Median intensity value of all the pixels contained within the object outline.

iii) Mode Intensity. Most common intensity value contained within the object outline.

iv) MTM Intensity—Median-based Trimmed Mean Intensity. Mean of all the pixels after removing pixels with intensity values that exceed four median absolute deviations (MADs; see below) above or below the median. This descriptor removes the influence of image artefacts (e.g., dust particles) on intensity estimation.

v) ARM Intensity—Artefact Removed Mean Intensity. Mean intensity of all the pixels in the object after removing pixels with intensity values greater than four median absolute deviations (MADs) above the median. This descriptor removes the influence of image artefacts on intensity estimation.

vi) Standard Deviation—The intensity value reported may be the mean of the pixel densities for an object outline or a standard deviation (SD) of pixel densities for each object outline.

vii) The Median of Absolute Deviation (MAD) is a descriptor of variation around the median intensity value (i.e., around the median intensity value of all the pixels contained within an object). It is the median of the absolute values of deviations from the median intensity (i.e., the absolute values of pixel densities—median intensity).

viii) ARM I×A—ARM Intensity (in current intensity unit) multiplied by area of the object (in current spatial unit). ARM Intensity is the mean of all the pixels in an object, after first removing pixels with intensity values that exceed four median absolute deviations (MADs) above the median, and replacing them with estimated values. Estimated values are derived by interpolation from neighbouring pixels.

II. Basic Morphometry Descriptors i) Area—Area is calculated by counting pixels inside object outline borders. Pixels underneath the border itself are not included.

ii) Perimeter—Perimeter is the length of the object's outer boundary.

iii) tPerimeter—Total perimeter. Length of the object's outer boundary plus the length around any inner holes or spaces contained within it.

iv) Clipped perimeter—Clipped perimeter is useful when object outlines touch the edge of the image. Pixels that touch the edge of the image are excluded from the perimeter calculation.

v) Clipped tPerimeter—Clipped total perimeter. Total perimeter minus the length of any border (inner or outer) that touches the edge of the image.

vi) Length—Length is the maximum distance across an object and is a descriptor that is allowed to cross object boundaries. In an S-shaped object, length is the straight line distance from tip to tip of the S.

vii) Feret diameters—Feret diameters are the maximum distances of the X (horizontal) and the Y (vertical) axes.

viii) Form factor—Form factor is a standard estimate of circularity that relates perimeter length to area. The more convoluted (and longer) the perimeter, the less circular the object. This descriptor varies from 0 and 1, with 1 being a perfect circle.

ix) The 8-shape descriptor. This descriptor is calculated as the ratio of minimal and maximal internal central chords of the object. The internal central chord is the segment located fully inside the object, based on the two pixels of object's border, and passing through the centre of gravity of the object. The algorithm finds shortest and longest internal central chords and returns their length ratio.

x) Weighted Relative Moment of Inertia—Index of the homogeneity of gray levels within a circular object. A value of 1 indicates the object is relatively homogeneous. If >1, the object has a higher proportion of bright pixels in its centre. If <1, the object has a higher proportion of bright pixels around its perimeter. This descriptor is also referred to as PDD, the peripheral intensity descriptor. It quantifies intensity concentration near an object's boundary. The object may be the nucleus, or the whole cell. PDD is defined by:

$$PDD = \frac{\sum_{i \subset O} U(r_i)|r_i|^2}{<U>_O \sum_{i \subset O} |r_i|^2} = \frac{\sum_{i \subset O} U(r_i)|r_i|^2}{<U>_O \cdot N \cdot R_g^2}$$

$U(r_i)$ is the intensity of the i-th pixel of the object O. $<U>_O$ and $R_g$ are the object's average intensity and gyration radius, respectively. Calculation of the PDD as described in the above equation involves the determination of centre of the object, by the object's centre of gravity. An alternative PDD, $PDD_2$, may be calculated according to:

$$PDD2 = \frac{\sum_i U(r_i^{border})|r_i^{border}|^\alpha}{<U>_O \sum_{i \subset O}|r_i^{border}|^\alpha}, \text{ where } \alpha < -1$$

PDD$_2$ is calculated based on border distance, not central distance: $r^{border}_i$ is the distance of a pixel from the object border, and $\alpha$, is an exponent controlling the sensitivity of the descriptor.

xi) Major Axis Length—Length of an object's major axis (i.e., the longer of two perpendicular axes of symmetry).

xii) Minor Axis Length—Length of object's minor axis (i.e., the shorter of two perpendicular axes of symmetry).

xiii) Major Axis Angle—Angle of object's major axis, relative to horizontal.

III. Chord Descriptors

The chord is the maximum distance (that does not cross a boundary) across the inside of an object. Both straight line and curvature-following chords are available.

IV. Diameter Descriptors

The diameter is an internal distance perpendicular to the curved chord. In circular objects, the chord and the diameter are identical. In elongated objects, the diameter is a descriptor of width and the chord is a descriptor of length.

i) Average Diameter—Mean internal distance perpendicular to the curved chord.

ii) Median Diameter—Median internal distance perpendicular to the curved chord.

iii) Maximum Diameter—Maximum internal distance perpendicular to the curved chord.

iv) Circular Diameter—Diameter of a circle whose area is equivalent to the area of the object.

The following descriptors (Related Object Descriptors and Related Fibre Descriptors) can be used to characterise the area of interest associated with the object under consideration. For example, for any single cell target C segmented in the image, one can define an area of interest (area of influence) IA(C), which is the set of pixels for which cell C is the closest cell. Then one could consider and quantify other segmented objects (e.g. grains, fibers) projected on IA(C), and use the obtained measurements for characterizing the cell C.

VI. Related Object Descriptors i) Count—The number of objects (e.g. grains) contained within the region of interest.

VII. Related Fibre Descriptors i) Fiber length—Total length within a single fibrous shape.

ii) End Nodes—Number end points in a single fibrous shape.

iii) Branch Nodes—Number of bifurcations within a single fibrous shape.

iv) Crossing Points—Number of intersections within a single fibrous shape. Bifurcations are not included.

v) Total Area Fiber Length—Total length of all fibrous shapes within a scan area.

vi) Total Area End Nodes—Total number of end points in all fibrous shapes within a scan area.

vii) Total Area Branch Nodes—Total number of bifurcations in all fibrous shapes within a scan area.

viii) Total Area Crossing Points—Total number of intersections in all fibrous shapes within a scan area. Bifurcations are not included.

ix) Fiber Relative Moment of Inertia—Relative descriptor of fiber dispersion within a single fibrous shape. A value of "1" indicates little or no branching away from the centre of the object. A value less than "1" indicates that branching occurs closer to the centre of the object. A value greater than one indicates that branching occurs further away from the centre of the object. The higher the number, the greater the distance from the centre.

VIII. User-Defined Descriptors

Descriptors may also be defined by a user using, for example, an equation editor to create novel descriptors.

Descriptors may also be derived from the properties of organelles in the cell cytoplasm. Other descriptors which may be used include the presence, absence or concentration of cellular features such as neurites, membrane ruffles, cytoplasmic granules, blebs, vesicles, vesicle clusters, cytoskeletal components.

In accordance with the descriptors defined above at least one of the measurements of the reference population image data, and of the target population image data, may relate to an intensity of the reference population image; and at least one of the measurements of the reference population image data, and of the target population image data, may relate to a morphological characteristic of one of the cells in the reference population.

Image Processing and Analysis

Figure 4:
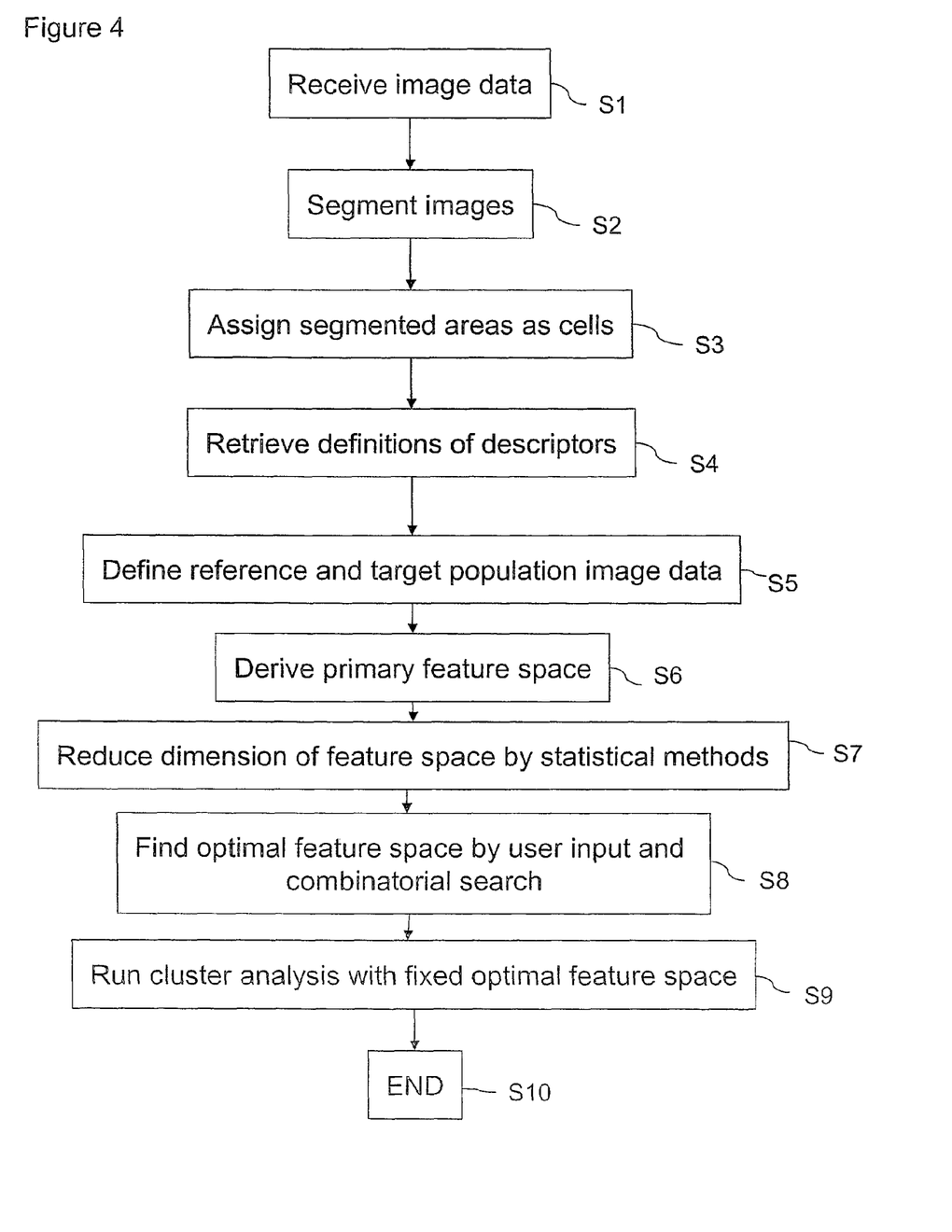
FIG. 4 is a flow diagram of steps of a method of performing image processing, in accordance with an embodiment of the present invention.

FIG. 4 is a flow diagram showing a number of steps of processing image data in accordance with an embodiment of the invention.

Image data which is recorded by the imaging system and which relates to the image of the reference population is received by the software system 18, and image data which is also recorded by the imaging system and which relates to the image of the target population is received by the software system 18, as shown in step S1.

In step S2, each image is segmented. In this step, areas of the images, which correspond to individual cells of the cellular sample, are distinguished from background areas of the cellular sample to identify cells of interest from the image data. The method of the present invention, in accordance with embodiments described below, does not depend on a specific segmentation routine, and may therefore apply any segmentation method that gives a reasonable segmentation result. For example, images may be segmented using techniques such as application of a top-hat algorithm, or using a seeded region growing technique which may use a particular parameter. It should be appreciated that further segmentation techniques may alternatively be used in accordance with the present invention.

Figure 5:
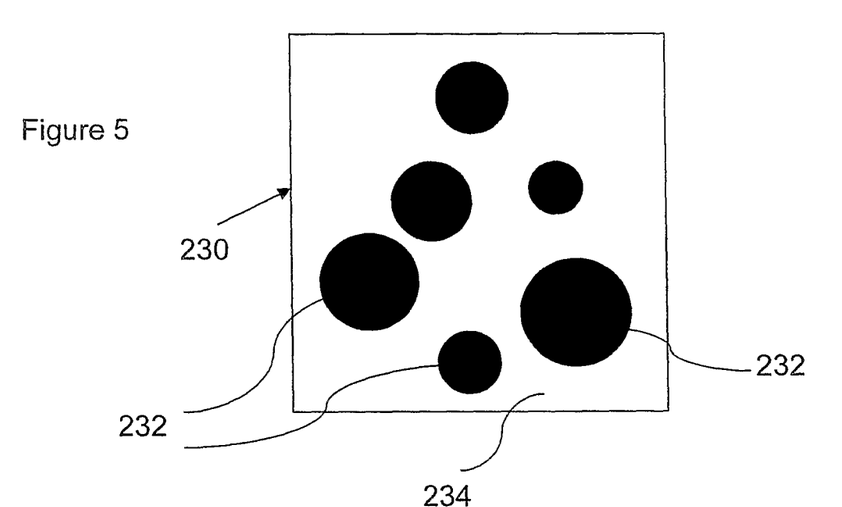
FIG. 5 shows schematically an image of biological objects according to an embodiment of the present invention.

In this example, to perform segmentation, a brightness threshold is first applied to the image data to identify relatively dark pixels and relatively light pixels of the image of the reference population and of the image of the target population. The level of the brightness threshold is set on the basis of areas of the image having different brightness intensities which are provided by, for example, biological markers. Such biological markers are described later in further detail. FIG. 5 shows an exemplary thresholded image 230 of either the reference population or the target population. Application of the threshold produces the thresholded image 230 which has areas of relatively dark pixels 232 which correspond with pixels of the recorded image having a brightness intensity below the threshold and areas of relatively light pixels 234 having a brightness intensity above the threshold.

With reference again to FIG. 4, the segmented object areas, having been identified, are assigned as cells in step S3. Next, definitions of the plurality of descriptors are retrieved in step S4 from the hardcoded routines 21. These include, in this embodiment of the invention, definitions of all of the descriptors described above in the section 'Available Descriptors'. Other selections of available descriptors are of course possible. Preferably, at least 20 different descriptors are available, more preferably at least 50 and yet more preferably at least 100.

In this embodiment, the reference population of cells and the target population of cells are defined in step S5 using image data of the reference population and of the target population, respectively.

In most cases, it is helpful to define at least some cells of the pivotal reference population of biological objects. However, in some cases the reference population might be essentially inhomogeneous, as it represents a mixture of physiological cellular states and their corresponding phenotypes. The definition of the reference population might involve one or several additional design steps of the method of the invention, such as annotation by a human operator of image data representing the reference population, definition of a sub-population of cells of the reference population, application of historical data of populations of cells to the image data, and/or the application of data from biophysical modelling to the reference population.

Similar techniques may be used to define cells of the target population of cells.

In further embodiments of the present invention, step S5 may be considered unnecessary.

Figure 6:
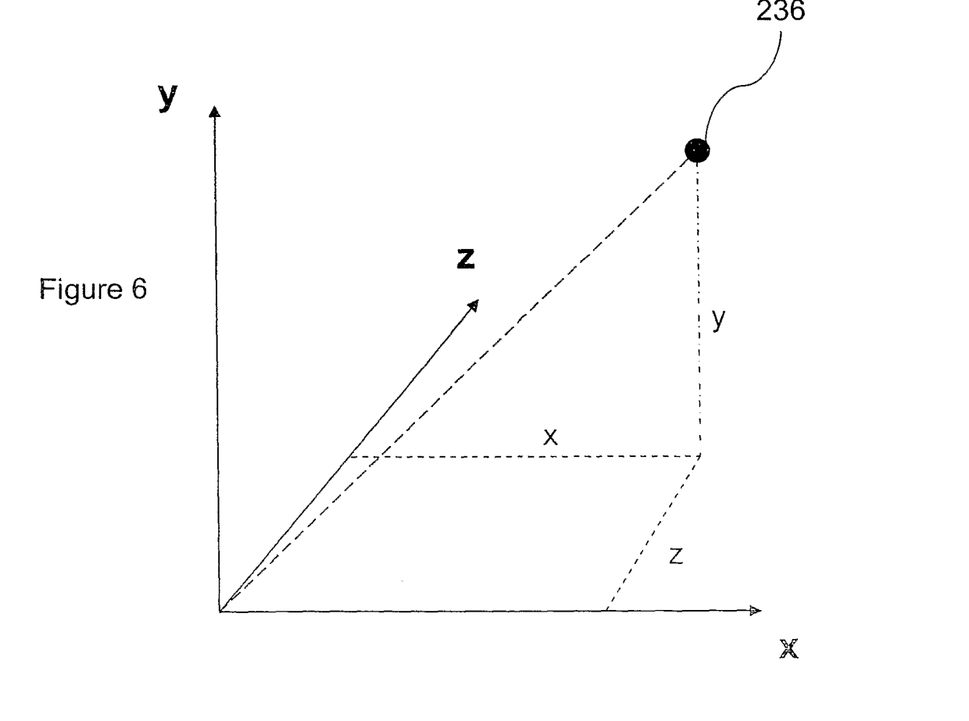
FIG. 6 shows a representation of a biological object in accordance with an embodiment of the present invention.

In step S6 a primary feature space is derived for the analysis of the target population. A reference set of descriptors is derived which comprises measurements in relation to the cells of the reference population. FIG. 6 shows a cell 236 represented by a feature vector in a three dimensional feature space. Each dimension corresponds with a different one of three orthogonal axes x, y, z.

In order to be technically comparable, both reference and target populations of cells must be rendered in the same feature space. In the cases when there is no prior knowledge about possible differences between reference and target sets of cells, the primary feature space should not be limited to a particular selection of descriptors. Therefore the primary feature space might be derived from all the descriptors available in the context of the problem, for example, classification of the target population. In many practical cases, however, some prior knowledge on the possible effect of the treatment applied to the cells of the target population is available. Such knowledge may be used to predict behaviour of cells of the target population. Such knowledge might be suggested by a user's expertise, or by historical data generated for a similar cellular application and derived from a database, where the data is available from published materials or from data modelling. In this way, therefore, some limitations on which descriptors form the primary feature space might be imposed at this stage. Such limitations, being made reasonably, could considerably reduce the dimensionality of primary feature space, which will result in speeding up of the analysis of the image data.

The target population image data is then processed with the reference set of descriptors to reduce the dimensions of the feature space using statistical methods, in step S7. In further embodiments of the present invention, step S7 may be performed as an alternative to, or in addition to, the step of optimising the feature space, step S8, described further below.

In this embodiment of the present invention, the reduction of the dimensionality of the primary feature space in step S7 is a necessary step. This step is aimed at the definition of an optimised, low-dimensionality feature space which is capable of use for effectively solving practical classification problems. The reduction of dimensionality can be done using a statistical analysis of the primary feature space descriptors, for example by using a factorial design, or by using a univariate statistical hypothesis testing applied to the descriptors. These procedures use the prior knowledge on what patterns belong to the reference and target populations. It can then be estimated how significant are the differences between each descriptor's statistics in the reference and target datasets, and what descriptors are providing an independent contribution to a separation between the reference and target populations. At this stage, the descriptors of the feature space that didn't pass hypotheses testing are excluded from the primary feature space.

In this embodiment, the feature space is next optimised, in step S8. This technique is related to the dimensionality reduction of the feature space described previously. This technique should be used in situations when the hypothesis-testing based dimensionality reduction wasn't effective and a user wants to reduce the dimensionality of the feature space even more, by specifying the desirable dimensionality $D_{min}$. The method relies on application of at least one inter-cluster separation measure. This will be explained using FIGS. 7 and 8.

Figure 7:
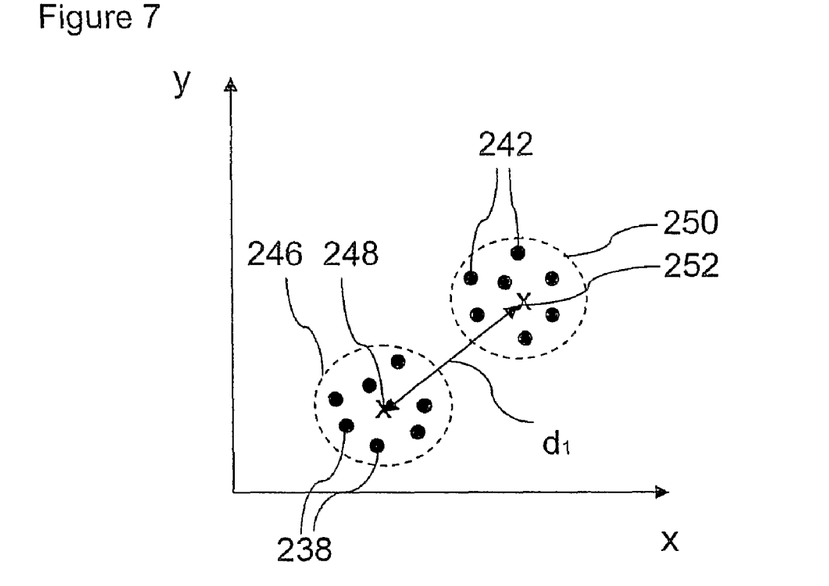
FIG. 7 shows a visualisation of populations of biological objects having a measure of difference, according to an embodiment of the present invention.

FIG. 7 shows a schematic visualisation of a two-dimensional feature space, prior to completion of the dimensionality reduction process. Each cell of the reference population is represented by a feature vector 238. These together form a reference set of vectors 238 which represent a reference population cluster 246. Each cell of the target population is represented by a different feature vector 242 and these vectors together form a target set of vectors 242 which represent a target population cluster 250. A distance $d_n$ between the centres of mass 248, 252 of the reference and target populations has a value of $d_1$ in this example. The distance $d_n$ might be defined in several possible ways by applying different metrics in multi-dimensional feature space. These metrics provide a measure of difference between the reference population and the target population and will be explained in more detail below. The inter-cluster separation measure can then serve, for example, as a parameter for a combinatorial search between different combinations of descriptors of the feature space, where each of these combinations has the dimensionality $D_{min}$. The combinatorial search proceeds until a preferred combination of descriptors is defined which gives the best inter-cluster separation, which in this example is a maximum of distance $d_n$.

Figure 8:
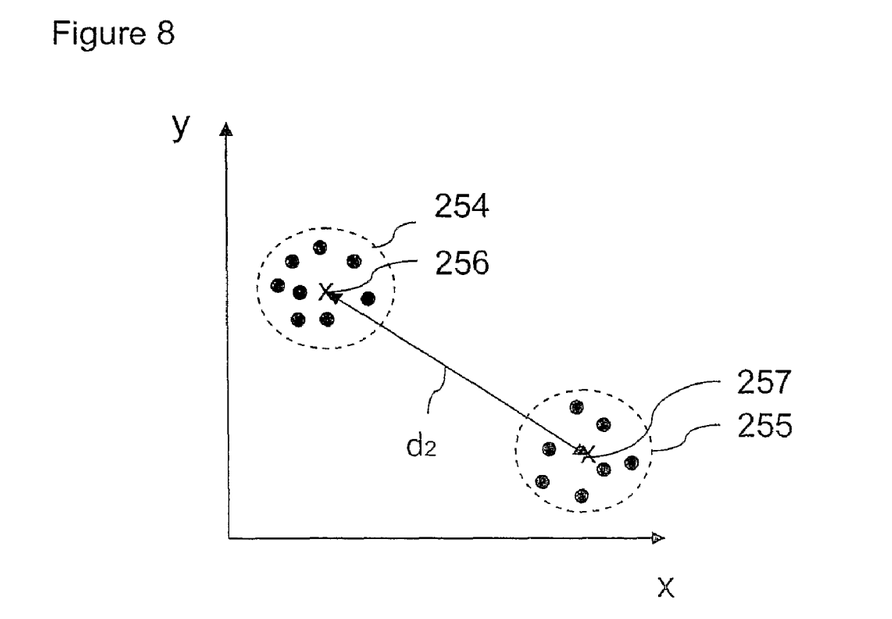
FIG. 8 shows a visualisation of populations of biological objects having a different measure of difference, according to an embodiment of the present invention.

Accordingly, FIG. 8 shows a further schematic visualisation of the reference and target populations in a two dimensional feature space, after completion of the dimensionality reduction process. The reference and target populations are represented by different clusters 254, 255. Further, the reference and target populations each have a modified centre of mass 256, 257 which are separated by a maximum distance $d_2$.

In the end of the dimensionality descriptor reduction process, the information on relevant descriptors, used for determining cells of the reference and target populations, can be stored in the data store 23 database as an update for the historical data on analysis specifications.

Further details of the dimensionality reduction technique and the inter-cluster separation measures may be in accordance with, but are not limited to, the techniques described by the following reference, the contents of which is included herein: Keinosuke Fukunaga, "Introduction to Stastistical Pattern Recognition", Second Edition, Academic Press, Inc., Boston San Diego New York London Sydney Tokyo Toronto, 1990, p. 447, p. 489.

Referring again to FIG. 4, an unsupervised clustering algorithm is next applied to the target population image data to perform an unsupervised cluster analysis, in step S9. At this stage, the feature space is considered fixed.

One example of the cluster analysis algorithm is a 'k-d tree based k-means clustering' algorithm which will now be described. K-means clustering is a popular clustering algorithm as it is simple and usually converges to a reasonable solution. The term k is a number of clusters to be identified. The k-means clustering algorithm comprises the following steps:

1. obtains the initial k statistical means. Each of these "means" may be a feature vector chosen by random in a close vicinity to the data's global centre of mass.

2. assigns each, in this embodiment, vector to its closest statistical mean among the k number of statistical means in order to update the membership of each vector to one of the k statistical means;

3. calculate each cluster's mean from the newly assigned vectors (this updates the centroid (mean) of k clusters); and 4. repeat step 2 and 3 of the k means clustering algorithm until a termination criteria is reached.

A common termination criteria is defined as the situation where, when repeating steps 2 and 3, none of the vectors change membership to a different cluster.

Once the cluster analysis is complete, the image data of the further population may be quantified to derive further measurements of particular descriptors for at least one of the patterns. These particular descriptors may not be descriptors of the preferred combination of descriptors, and may be particular measurements desired by a user.

The patterns of the further population which are identified from the further population image, according to the present invention, may be compared with identified patterns from the further population image using a different image processing technique. Thus, the identification of patterns in accordance with the present invention may be validated.

The method of the present invention has been described in relation to identifying patterns of one further population. The method of the present invention may be used to identify cells of two or more further populations of biological objects.

An example implementation of the method of the present invention will now be described where cells of two further populations are identified.

Example Implementation

In this example an image of a G1S Cell Cycle Phase Marker Assay was recorded and the corresponding image data were processed in order to identify cells being in either S-phase or a complement S-phase. The G1S Cell Cycle Phase Marker Assay is available from GE Healthcare Bio-Sciences (product number 25-9003-97) and is the subject of international patent publication number WO 2006/008542.

The G1S Cell Cycle Phase Marker sensor has been developed using functional elements from the human helicase B gene fused to Enhanced Green Fluorescent Protein (EGFP). In G1-phase cells, the sensor protein is predominantly localized within the nucleus. However, increasing Cdk2/cyclin E activity phosphorylates the sensor late in G1. Consequent exposure of a nuclear export sequence causes the sensor to translocate to the cytoplasm prior to S-phase entry. Cell cycle status can be determined by interrogating the subcellular location and intensity of the green fluorescent protein.

The G1S Cell Cycle Phase Marker Assay enables dynamic examination of cell-cycle phases in individual cells. The assay provides a live cell, non-perturbing sensor of Cdk2/cyclin E activity and is an indicator of G1- and S-phases of the cell cycle. In conjunction with fluorescence microscopy, subcellular translocation of the G1S Cell Cycle Phase Marker Assay can discriminate the phase-specific cell-cycle position of individual cells within an asynchronous population.

A preferred combination of descriptors was defined in accordance with the present invention to provide the best measure of difference between sets of measurements in relation to cells of the S-phase and sets of measurements in relation to cells of the complement S-phase. This gave the best clustering of the sets of measurements for the S-phase cells and the best clustering of the sets of measurements for the complement S-phase cells.

The preferred combination of descriptors included a descriptor relating to the intensity in the sample image of a nuclear region of the cells and a descriptor relating to the intensity in the sample image of a cytoplasmic region of the cells. Sets of measurements for the sample cells were derived having the preferred combination of the descriptors. For the S-phase cells, measurements for each of the two preferred descriptors were different to measurements for each of the two descriptors for cells of the complement S-phase, due to translocation of the Helicase B molecule in the cells.

By applying the k-means clustering algorithm to the sets of measurements, cells of the sample population were classified as cells in the S-phase, and cells of the sample population were classified as cells in the complement S-phase.

The classification was verified using a nuclear marker BrDU in the sample cells.

The above embodiments are to be understood as illustrative examples of the invention. Further embodiments of the invention are envisaged.

In further embodiments of the present invention, a user may provide input, for example using a graphical interface. The user may provide input which improves definition of the preferred combination. For example, the user may select an image processing mode which specifies a type of cellular assay being performed, such as a translocation assay mode or a vesicle formation mode. For embodiments described above, the reference set and the target set of measurements may be initially derived for all of the plurality of descriptors for which definitions are stored in the descriptor data store. Selecting a particular processing mode may select definitions of only a proportion of the descriptors rather than all of the descriptors, for initial derivation of the reference set and target set of measurements. In this way the proportion of descriptors initially selected may be more suited to processing an image for a particular type of assay. Moreover, by initially selecting less than all of the descriptors, the image and data processing may be simplified and the definition of the preferred combination may thus be more efficient and faster.

A user may also provide input during selecting the combination of descriptors and during comparing of the sets of measurements to improve definition of the preferred combination. Further, a user may provide input during the cluster analysis algorithm in order to improve identification of clusters of cells.

The user may also provide a definition of a similarity of cell population characteristics and/or a definition of a similarity of population areas of feature space.

Once the cells have been clustered, a user may inspect the clusters and assign a meaningful classification label to each of the clusters of cells. The label may be appropriate to phenotypical characteristics of the cells and/or physiological meanings of the cells In addition to user input, the imaging system may access a data store in order to retrieve historic cell population data which has been previously generated for cellular assays and/or cell population data published by third party sources.

The present invention is not limited to using fluorescence imaging to obtain image data of cellular images. Brightfield imaging, DIC imaging or phase contrast imaging may alternatively be used.

Prior to segmenting the image, pre-processing algorithms may be applied to the image, such as flat field correction, de-noising and de-shading. Post-processing algorithms may also be applied before segmentation, including sieving, object de-clumping, tessellation, and erosion or dilation of the segmented image objects.

For embodiments described above each biological object is a biological cell. It is envisaged that the biological objects may alternatively be other biological objects, for example sub-cellular biological objects such as cell nuclei.

When obtaining the image data described above, the cells and/or cellular components are identified by the imaging system using emissions of biological markers. For example, a nuclear marker, producing fluorescence at a certain wavelength may be used to identify nuclear areas for each cell in an image. The nuclear marker may be an intercalating nuclear dye, such as a Hoechst™ dye, for example Hoechst 33342 manufactured by Invitrogen, or may be in the form of an NLS-fluorescent protein fusion such as the Clontech™ pHcRed1-Nuc vector which produces a red fluorescence signal.

Assays of the present invention may make use of any known fluorophore or fluorescent label including but not limited to fluorescein, rhodamine, Texas Red, GE Healthcare Bio-Sciences stains Cy3, Cy5, Cy5.5 and Cy7, DRAQ5™ manufactured by Biostatus, and Coumarin stains (See Haugland, R. P., Handbook of Fluorescent Probes and Research Chemicals 6$^{th}$ Ed., 1996, Molecular Probes, Inc., Eugene, Oreg.).

In deriving the measurements of the descriptors, binary masks which define the object areas of the image, within which the measurements are to be taken, may be generated, such as an eroded nuclear mask and a thin cytoplasmic ring. Object areas may be identified which each correspond to a nucleus of a cell. Eroding each nuclear object area from the edge, by a predetermined number of pixels, generates the eroded nuclear mask. Object areas may be identified which each correspond to a cytoplasm of a cell. A thin cytoplasmic ring, representing the cytoplasmic area of a cell adjacent to the nucleus, may be generated by dilating the nuclear object area from its edge by a predetermined number of pixels.

Further descriptor definitions in relation to nuclear and cytoplasmic regions of the cells, which may be selected in accordance with the example implementation, are given below:

$I_n$, Fluorescence signal intensities in each pixel in the eroded nuclear mask area are averaged to produce a measurement of the average nuclear signal intensity ($I_n$) descriptor which represents the average intensity over the nuclear area;

$I_c$, The fluorescence signal intensities in each pixel in the thin cytoplasmic ring are averaged to produce measurement of the average cytoplasmic signal intensity ($I_c$) descriptor representing the average intensity within cytoplasmic sampling ring;

I×A—Intensity×Area. Mean intensity (in current intensity unit) within the object outline multiplied by its area (i.e., 1×A=total intensity within the object outline). This descriptor may be used to estimate "total signal" intensity associated with a given object. This descriptor may also be referred to as the Nuclear Flux or integrated intensity ("Power"), which is defined as the sum of nuclear channel intensities of all pixels of the nuclear mask. In "wide-field" (non-confocal) microscopy, the Nuclear Flux is approximately proportional to the number of fluorescent molecules residing in the nucleus.

$A_{nuc}$, the area of the cell nucleus;

$A_{nuc}/A_{cell}$, the ratio of the area of the nucleus to the size of the cell;

$(W/L)_{nuc}$, the nuclear elongation (ratio of the lengths of the nucleus in the major and minor axes);

$P_{nuc}^2/4\pi A_{nuc}$ the form factor of the nucleus, which is equal to 1 for a perfectly round nucleus;

$P_{nuc}^2/4\pi A_{cell}$, the form factor of the cell, which is equal to 1 for a perfectly round nucleus;

$D/R_{g\ nuc}$, the nuclear displacement. D is the distance between the nucleus' and the cell's centres of gravity, and $R_{g\ nuc}$ is the gyration radius of the nucleus. Gyration radius of an object composed of N pixels is defined by:

$$R_g^2 = \frac{1}{N}\sum_{i=1}^{N}(r_i - r_{CG})2$$

$$r_{CG} = \frac{1}{N}\sum_{i=1}^{N}r_i$$

where $r_i$ denotes the coordinates of the i-th pixel in the object, and $r_{CG}$ denotes the coordinates of the centre of gravity;

$LIR_{N/C}=I_N/I_C$, (Local Intensity Ratio). The ratio of the two measured average intensities $I_n$, $I_c$ is taken to generate the nuclear/cytoplasmic ratio ($I_n/I_c$) quantifier, representing the ratio of nuclear and cytoplasmic average intensities.

$LIR_{C/Bckg}$, the ratio of cell intensity to the intensity of the background sampled in the immediate vicinity of the cell. The background vicinity may be determined by dilating a binarized image of the cell, and then excluding the cell according to its original size from this dilated image;

$CV_{nuc}$ the ratio of the standard deviation/mean of the nuclear intensity; and $CV_{cyt}$, the ratio of the standard deviation/mean of the cytoplasmic intensity.

For embodiments described above, it is envisaged that a combination of descriptors may be selected which includes descriptors which are different to the descriptors explained above. Further descriptors may be defined in relation to a ratio between any of the descriptors mentioned. The properties of chromosomes within the nucleus (e.g. chromosome condensation) may also be used as a source of descriptors.

As mentioned above, various types of metrics providing measures of difference are available for use in defining the preferred combination of descriptors. Examples of such measures of difference will now be described below; however, further types of measures of difference, not described, may alternatively be used in accordance with the present invention. Some of the measures are defined using the term $d_n$, which is a measure of difference based on a distance, and the terms $x_1$ and $x_2$ which correspond with two vectors whose similarity is to be determined.

I. Euclidean distance.

The Euclidean distance is defined as:

$$d_e = \sqrt{\sum_{i=1}^{D} (x_1^{(i)} - x_2^{(i)})^2} \,,$$

where the summation index i is the index of descriptor running from 1 (the index of the first descriptor of the feature vector) to D (the index of the last descriptor of the feature vector). D equals to the dimensionality of the feature space.

The Euclidean distance measure has the property of giving greater emphasis to larger differences on a single descriptor. The classification can thus be biased towards a descriptor with dominant values. To overcome this problem, descriptor measurements can be normalised and/or otherwise weighted using known statistical techniques prior to creating a feature vector.

II. City Block or Interpoint Distance

The city block distance ($d_{CB}$) is also known as the absolute value distance or 'Manhattan' distance. The city block distance is computationally cheaper to calculate than the Euclidean distance and allows a relatively high speed of processing to be performed. The city block distance is defined as:

$$d_{CB} = \sum_{i=1}^{D} |x_1^{(i)} - x_2^{(i)}|.$$

III. Chebyshev Distance

The Chebyshev distance ($d_{Ch}$) measure of difference is also computationally cheaper than the Euclidean distance. It is defined as:

$$d_{Ch} = \max_{i} |x_1^{(i)} - x_2^{(i)}|.$$

IV. Mahalanobis Distance

The Mahalanobis distance is used for estimating the proximity $\|x, \text{Cluster}(j)\|$ between some pattern x (e.g. feature vector representing biological cell) and the j-th cluster of patterns (e.g. the set of feature vectors representing the j-th population of biological cells), in the feature space. It is supposed that the multi-dimensional probability density distributions are normal for all clusters, and clusters are statistically equivalent, i.e. there is no prior information on clusters. This "partial" vector-to-cluster distance is defined as:

$$\|x, \text{Cluster}(j)\| = \sqrt{\frac{1}{2}\ln|\Sigma_j| + (x - m_j)^T \Sigma_j^{-1} (x - m_j)}\,.$$

where the terms $m_j$ and $\Sigma_j$ are the mean and the covariation matrix of the j-th cluster, respectively. Further details are incorporated by way of the following reference: Keinosuke Fukunaga, "Introduction to Stastistical Pattern Recognitiopn", Second Edition, Academic Press, Inc., Boston San Diego New York London Sydney Tokio Toronto, 1990, page 169; the contents of which is incorporated herein. The Mahalanobis distance automatically accounts for the scaling of the axes of the feature space, and corrects for correlation between related descriptors (descriptors whose measurement values are to a degree interdependent). Computational requirements for the Mahalanobis distance metric grow quadratically with the number of descriptors.

As a simplified analogue of Mahalanobis distance, determining a measure of difference between the centres of mass described above, the inter-cluster distances may be corrected (normalized) by using a degree of variance of clusters.

Use of a k-means clustering algorithm is described to identify categories of cells. Alternative clustering algorithms may be used. Further, it is envisaged that alternative methods of identifying categories of cells may instead be used.

An example of implementation in accordance with the present invention is described with relation to a nuclear S-phase and a nuclear complement S-phase of cells. Applications of the present invention are not limited to identification of cells in these nuclear phases. It is envisaged that identification of cells in alternative nuclear phases may be provided. For example, cells in a prophase, metaphase, anaphase, telophase, G2 and/or G2 nuclear phase may be identified. Further, the present invention is not limited to identifying cells with a particular nuclear phase. Cells having different identifying characteristics may alternatively be identified.

The given environments of the populations of cells may be different to those described above and the treatment agent may instead be a physical treatment agent, or a non-medical chemical compound.

The present invention is useful for identifying pharmacological agents for the treatment of disease. It provides a potentially automated, high throughput method of conducting a wide variety of biological assays. Such assays can be conducted on chemical compounds or any molecule of biological interest, including but not limited to drug candidates, such as those found in combinatorial libraries, allowing high throughput screening of chemical compounds of biological interest.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A computer-implemented method of performing image processing for images of biological objects, said method comprising:
   a) storing definitions of each of a plurality of descriptors for which measurements can be taken in relation to said biological objects;
   b) receiving image data relating to an image of a reference population of biological objects exposed to a given biological environment;
   c) receiving image data relating to an image of a target population of biological objects exposed to a different given biological environment;
   d) processing said reference population image data to obtain a reference set of measurements, containing data for each of said plurality of descriptors;
   e) processing said target population image data to obtain a target set of measurements, containing data for each of said plurality of descriptors; and
   f) selecting a combination of one or more of said plurality of descriptors on the basis of comparing said reference measurement data with said target measurements data to define a preferred combination of said descriptors for use in identifying characteristics of a further population of biological objects which are similar to those of the target population.

2. The method of claim 1, further comprising:
g) modifying said sets of measurements, by changing the selected combination of descriptors,
h) comparing respective ones of said plurality of reference sets of measurements with corresponding ones of said plurality of target sets of measurements to determine a plurality of measures of difference between said reference population and said target population; and
i) comparing said measures of difference determined in step h) to select said preferred combination of said descriptors.

3. The method of claim 1, wherein a measure of difference between said reference population and said target population is maximised for a set of measurements of said reference population with said preferred combination of descriptors.

4. The method of claim 1, wherein at least one of said measurements relates to an intensity of said image of said reference population or to an intensity of said image of said target population.

5. The method of claim 1, wherein at least one of said measurements relates to a morphological characteristic of said objects in said image of said reference population or to a morphological characteristic of said objects of said target population.

6. The method of claim 1, wherein selecting the combination in step f) includes excluding at least one of said plurality of descriptors from said combination selected in step f), using said reference population measurements and said target population measurements, so that said preferred combination excludes at least one descriptor.

7. The method of claim 1, wherein said target population has been treated with a treatment agent and said reference population has not been treated with said treatment agent.

8. The method of claim 7, wherein said reference population is a control population of biological objects.

9. The method of claim 1, wherein each said biological object is a biological cell.

10. The method of claim 1, further comprising:
j) receiving further image data relating to an image of a further population of biological objects exposed to a given environment;
k) processing said further population image data to derive a set of measurements with said preferred combination of said descriptors; and
l) processing said set of measurements for said further population to identify characteristics which are similar to those of said target population.

11. The method of claim 10, wherein said processing in step l) includes classifying said objects of said further population.

12. The method of claim 11, wherein said processing in step l) includes identifying a cluster of said objects of said further population for said classification.

13. The method of claim 1, wherein a user provides input which is used to define said preferred combination of said descriptors.

* * * * *